United States Patent
Zumpano

(10) Patent No.: US 10,561,731 B2
(45) Date of Patent: Feb. 18, 2020

(54) METHOD AND COMPOSITIONS FOR SOLUBILIZING NON-POLAR CONSTITUENTS

(71) Applicant: Entourage Bioscience, LLC, Fairfiled, CA (US)

(72) Inventor: Michael V. Zumpano, Fairfield, CA (US)

(*) Notice: Subject to any disclaimer, the term of this patent is extended or adjusted under 35 U.S.C. 154(b) by 0 days.

(21) Appl. No.: 16/503,893

(22) Filed: Jul. 5, 2019

(65) Prior Publication Data

US 2019/0328883 A1 Oct. 31, 2019

Related U.S. Application Data

(62) Division of application No. 15/433,649, filed on Feb. 15, 2017, now Pat. No. 10,376,586.

(60) Provisional application No. 62/295,510, filed on Feb. 16, 2016.

(51) Int. Cl.

| | | |
|---|---|---|
| *A61K 47/14* | (2017.01) | |
| *A61K 31/05* | (2006.01) | |
| *A61K 9/00* | (2006.01) | |
| *A24B 15/16* | (2006.01) | |
| *C07D 475/02* | (2006.01) | |
| *C07D 239/42* | (2006.01) | |
| *A61K 31/506* | (2006.01) | |
| *A61K 31/525* | (2006.01) | |
| *A24B 15/167* | (2020.01) | |
| *A61M 15/00* | (2006.01) | |

(52) U.S. Cl.
CPC ............ *A61K 47/14* (2013.01); *A24B 15/167* (2016.11); *A61K 9/007* (2013.01); *A61K 31/05* (2013.01); *A61K 31/506* (2013.01); *A61K 31/525* (2013.01); *C07D 239/42* (2013.01); *C07D 475/02* (2013.01); *A61M 15/00* (2013.01)

(58) Field of Classification Search
CPC ....... A61K 47/14; A61K 31/05; A24B 15/167
See application file for complete search history.

(56) References Cited

U.S. PATENT DOCUMENTS

| | | | |
|---|---|---|---|
| 10,376,586 B2 * | 8/2019 | Zumpano | C07D 475/02 |
| 2007/0104741 A1 | 5/2007 | Murty | |
| 2008/0159961 A1 | 7/2008 | Woolfe et al. | |
| 2012/0058158 A1 | 3/2012 | Booles | |
| 2015/0181924 A1 | 7/2015 | Llamas | |
| 2015/0342902 A1 | 12/2015 | Vangara et al. | |

OTHER PUBLICATIONS

"Captex 300", Jul. 13, 2007.
Rayner, Marilyn , et al., "Quinoa starch granules as stabilizing particles for production of Pickering Emulsions," vol. 158, pp. 139-155, 2012.
Solowij, Nadia , et al., "A protocol for the delivery of cannabidiol (CBD) and combined CBD and delta-tetrahydrocannabinol (THC) by vaporisation", 2014, vol. 58, pp. 1-8.
MIGLYOL(R) 810, 812 (Cremer Oleo, Mar. 2013, pp. 1-7, 2013.

* cited by examiner

*Primary Examiner* — James D. Anderson
(74) *Attorney, Agent, or Firm* — Durham, Jones & Pinegar; Sarah Matthews

(57) ABSTRACT

A method for solubilizing non-polar target compounds into a carrier liquid is described. A carrier oil, such as a MCT, or a mixture of MCTs, may be used to solubilize non-polar target compounds. The carrier oil may also include one or more buffers for stability of the target compounds within the carrier oil.

19 Claims, No Drawings

METHOD AND COMPOSITIONS FOR SOLUBILIZING NON-POLAR CONSTITUENTS

BACKGROUND OF THE INVENTION

State of the Art

The present disclosure relates to a method which may be used to solubilize non-polar constituents. The disclosure also relates to the solutions/compositions formulated via the subject solubilization process, to the method for preparing same, to the resulting compositions containing the non-polar constituents thus solubilized, and to the administration thereof.

Electronic nicotine delivery systems (ENDS) have grown in popularity in recent years. In 2014, ENDS usage surpassed traditional cigarette usage in young people in the United States. Hildick-Smith, Gordon J.; Pesko, Michael F.; Shearer, Lee; Hughes, Jenna M.; Chang, Jane; Loughlin, Gerald M.; Ipp, Lisa S. (2015). "A Practitioner's Guide to Electronic Cigarettes in the Adolescent Population." *Journal of Adolescent Health*, 57: 574-9. Most commonly, ENDS work by heating a liquid to its boiling point, vaporizing the liquid for the user to inhale.

Typically, the carrier liquid used in ENDS consists of a combination of vegetable glycerin and propylene glycol, along with a "flavor," and/or nicotine. Flavors or additives known in the art are limited to those which may be solubilized in vegetable glycerin or a combination of vegetable glycerin and propylene glycol. Additives may also be limited by their boiling point, as a compound with a high boiling point can create an uncomfortable hot vaping experience in order to vaporize the compound.

While it may be desirable to have additives that are non-polar or strongly non-polar, there are currently no known methods in the art for solubilizing such compounds within the known carrier liquid, as vegetable glycerin and propylene glycol are both polar compounds. Additionally, although propylene glycol may have emulsifying qualities, its hydrophilic-lipophilic balance may be insufficient to stabilize many non-polar compounds.

SUMMARY OF THE INVENTION

The present disclosure may provide a method to solubilize target compounds, such as non-polar compounds, in a carrier liquid for use in ENDS.

The present disclosure includes multiple different methods, systems, and applications which can be used to solubilize non-polar target compounds and are thus applications of a common inventive concept. It should be appreciated that various devices, systems, methods and applications will have some benefits and may lack other benefits which are present in different devices, systems, methods and applications. Therefore, the teachings of the present disclosure and any actual or intended benefit of any embodiments should not be read into the claims unless expressly stated therein.

According to one aspect of the present disclosure, the carrier liquid to be used to solubilize the target compound may comprise a mixture of different types of medium chain triglycerides (MCT), in the range of C6-C12. The target compound may be any suitable non-polar compound and in some aspects, the non-polar compound is one of riboflavin, sulbutiamine, and cannabidiol.

According to one aspect, a method is described to solubilize non-polar target compounds, the method comprising admixing a medium chain triglyceride carrier liquid and a non-polar target compound. Mixing the medium chain triglyceride carrier liquid and the non-polar target compound may form an azeotropic mixture, which may allow a lower, more pleasant temperature of vaporization, and may allow a cleaner vaporization for improving the useful life of the device.

According to another aspect, the carrier liquid and the non-polar target compound may be mixed in several different ratios, depending on the target compound. For example, the carrier liquid and the non-polar target compound may be mixed in a ratio of about 0.01:99.99. Or the carrier liquid and the non-polar target compound may be mixed in a ratio of about 95:5, or mixed in a ratio of about 50:50.

In some configurations, the medium chain triglyceride carrier liquid may comprise a mixture of C6-C12 medium chain triglycerides. For example, the medium chain triglyceride carrier liquid may be comprised of at least one of approximately 0-6.0% hexanoic acid, 6.0-60% octanic acid, and 6.0-60% decanoic acid, where the medium length fatty acids may be incorporated into the glycerol backbone of the triglyceride.

According to another aspect, the method may further comprise adding an amount of buffer to the carrier liquid. Similarly, the method may comprise adding an amount of acid to the carrier liquid, or adding an amount of two or more buffers to the carrier liquid. The buffer may have a molar concentration of around 0.01-10 mM in the carrier liquid.

Also disclosed herein is a composition for use in an electronic nicotine delivery system, the composition comprising a non-polar target compound and a carrier liquid comprised of one or more medium chain triglycerides. The composition may comprise approximately 0.01 to 70 percent non-polar target compound and 30 to 99.99 percent carrier liquid. Other percentages are possible as well. For example, 30 to 70 percent non-polar target compound may be use with 70 to 30 percent carrier liquid.

The non-polar target compound of the composition may comprise essential oils, for example, monoterpenes, triterpenes, sesquiterpenes, and/or diterpenes. According to another configuration, the non-polar target compound may comprise at least one of riboflavin, sulbutiamine, and cannabidiol.

According to another aspect of the disclosure, the carrier liquid of the composition may comprise a mixture of at least one or more of triglycerides composed of one or more of the following fatty acids (on a glycerol backbone to form the triglyceride): hexanoic acid, octanic acid, decanoic acid, and dodecanoic acid. In some compositions, the carrier liquid may comprise about 0-6 percent triglycerides composed of hexanoic acid, 6-60 percent triglycerides composed of octanic acid, and 6-60 percent triglycerides composed of decanoic acid.

Small amounts, such as 0.00% to 30% of branched-chain fatty acids, such as lanolin, may be added in order to increase viscosity. Lanolin contains a high proportion of iso and ante/so fatty acids from $C_{10}$ to $C_{34}$ in chain length including an ante/so-branched fatty acid, 18-methyl-eicosanoic acid, which constitutes up to 60% of the total fatty acids.

According to yet another aspect, a vapor cartridge is disclosed containing a composition comprising a non-polar target compound and a carrier liquid comprised of one or more medium chain triglycerides. The cartridge may further comprise a wick, such as a cotton wick or other type of wick, or non-wick vaporization system.

These and other aspects of the present invention are realized in a method for solubilizing non-polar constituents as shown and described in the following figures and related description.

DETAILED DESCRIPTION

The skilled artisan will understand that the methods described below can be practiced without employing these specific details, or that they can be used for purposes other than those described herein. Indeed, they can be modified and can be used in conjunction with products and techniques known to those of skill in the art in light of the present disclosure.

Reference in the specification to "one configuration," "one embodiment" "one aspect" or "a configuration," "an embodiment" or "an aspect" means that a particular feature, structure, or characteristic described in connection with the configuration may be included in at least one configuration and not that any particular configuration is required to have a particular feature, structure or characteristic described herein unless set forth in the claim. The appearances of the phrase "in one configuration" or similar phrases in various places in the specification are not necessarily all referring to the same configuration, and may not necessarily limit the inclusion of a particular element of the invention to a single configuration, rather the element may be included in other or all configurations discussed herein. Thus it will be appreciated that the claims are not intended to be limited by the representative configurations shown herein. Rather, the various representative configurations are simply provided to help one of ordinary skill in the art to practice the inventive concepts claimed herein.

Furthermore, the described features, structures, or characteristics of embodiments of the present disclosure may be combined in any suitable manner in one or more embodiments. In the following description, numerous specific details may be provided, such as examples of products or manufacturing techniques that may be used, to provide a thorough understanding of embodiments of the invention. One skilled in the relevant art will recognize, however, that embodiments discussed in the disclosure may be practiced without one or more of the specific details, or with other methods, compounds, materials, and so forth. In other instances, well-known structures, materials, or operations may not be shown or described in detail to avoid obscuring aspects of the invention.

Before the present invention is disclosed and described in detail, it should be understood that the present invention is not limited to any particular structures, process steps, or materials discussed or disclosed herein. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of that aspect in the claims.

It should also be noted that, as used in this specification and the appended claims, singular forms such as "a," "an," and "the" may include the plural unless the context clearly dictates otherwise. Thus, for example, reference to "a bracket" may include an embodiment having one or more of such brackets, and reference to "the target plate" may include reference to one or more of such target plates.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The invention and will now be so as to enable one skilled in the art to practice the present invention. The descriptions are intended to be exemplary of various aspects of the invention and are not intended to narrow the scope of the appended claims.

As used herein, "electronic nicotine delivery system" or "ENDS" means any type of device that may be used to vaporize a solution for inhalation of the vapors, whether or not the solution contains nicotine. Such systems include, for example, electronic cigarettes, vaping devices, advanced personal vaporizers, etc.

As used herein, "MCT" or "MCTs" means medium-chain triglycerides. It may refer to one type of medium-chain triglyceride, or it may refer to a mixture of different types of medium-chain triglycerides. For example, it may refer to a solution of a single type of medium-chain triglyceride of a particular length, or it may refer to a mixture of medium-chain triglycerides with different compositions and/or lengths.

As used herein, the term "target compound" means a compound to be added to a carrier liquid or carrier oil to be used in an ENDS. The target compound may be a non-polar compound. For example, target compounds may comprise non-polar essential oils, non-polar compounds that exist as solids at room temperature, compounds that are insoluble in vegetable glycerin and propylene glycol, compounds that vaporize at a higher temperature than vegetable glycerin and propylene glycol, and compounds that form an azeotrope with medium-chain triglycerides. Essential oil target compounds may include monoterpenes, diterpenes, and sesquiterpenes.

As used herein, "carrier oil" or "carrier liquid" refers to the liquid used to solubilize the target compound. Carrier oil and carrier liquid are used interchangeably herein. The carrier oil may comprise a mixture of different MCTs, such as a mix of C6-C12 MCTs, or it may comprise a single type of medium-chain triglyceride. The carrier liquid may have other additives, such as additives that increase the stability of the carrier liquid. A variety of MCTs may be used, such as MCT formed from 2 or 3 of the fatty acid chains attached to glycerol which are of medium length. Both branched and unbranched fatty acids may be used, as well as saturated and unsaturated. Typically, 2 to 3 chains of the medium chain tryglyceride may be hexanoic acid, octanoic acid, decanoic acid, and/or dodecanoic acid.

As used herein, "solubilization of a target compound" means a dispersion in the molecular state in a carrier liquid.

Solubilization of target compounds may be achieved by the use of a carrier liquid that is azeotropic with the target compounds. Standard azeotropes have a boiling point either higher or lower than any of its individual components. Most commonly for the present disclosure, the azeotropes have a lower boiling point than their components. Additionally, an azeotrope retains the same composition in the vapor state as in the liquid state. By using an azeotrope, the temperature at which the target compound may be vaporized is lowered. This may allow target compounds to be used in ENDS which would otherwise vaporize at a temperature that was too high. Additionally, the azeotrope is suitable for use in an ENDS because the proportions of the constituents of the composition of the liquid state and the vapor state are the same.

In order to form an azeotrope with the target compounds, different types of carrier liquids may be used. For example, blends of medium-chain triglycerides, formed of medium-chain fatty acids with aliphatic tails of 6-12 carbons, were found to be azeotropic with many target compounds. Depending on the desired results, different blends of the medium-chain triglycerides may be used. For example, triglycerides formed of medium-chain fatty acids with aliphatic tails of 6 carbons (C6 triglycerides) may be desirable as a low molecular weight oil that may decrease the viscosity and modify the flow rate through the wick of the ENDS, improve the stability of dissolved target compounds against temperature changes, and/or improve the solubility of target compounds. Thus, a blend that includes some C6 triglycerides, between 0.01% and 30%, along with other MCTs, may be beneficial, compared to using entirely C6 triglycerides.

Varying the proportion of chain-length of the triglyceride varies the viscosity of the carrier oil. An oil that lacks proper viscosity may leak from the ENDS, and one that is too viscous may cause wick starvation. Varying the concentrations or proportions of different chain-lengths of triglycerides may allow for tailoring of a carrier oil that has a good flow rate that minimizes prevents wick starvation and leakage from the ENDS.

The amount of target compound and the amount of carrier fluid may also be varied. For example, a mixture of approximately 50/50 target compound/carrier fluid has been found to be azeotropic with a lower boiling point. Other concentrations may also be used. For example, a mixture of 5/95 target compound/carrier fluid may be azeotropic, as well as a mixture of 60/40 target compound/carrier fluid. According to another aspect of the present disclosure, a component may be added to the carrier liquid/target compound mixture in order to provide stability. This may be necessary, for example, when using target compounds that contain carboxylic functional groups. Carboxylic acids have labile hydrogen atoms which can dissociate and leave the molecule in a more polar ionized state. These ionized or "activated" carboxylic acids can be retained on certain types of wicks, including cotton or synthetic wicks, which are common in the vape market. This can inhibit the flow of the molecules containing a carboxylic acid into the heating chamber, and can also lead to the accumulation of the molecules on the wick, which inhibits flow. By adding a stabilizing compound, the labile hydrogen atoms may be more stabilized, preventing ionized carboxylic acids that may be retained on wicks.

It is well known that when organic acids are in an environment that is more than 2 points of pH above their $pK_a$ they will be greater than 99% ionized and therefore, more polar and more likely to be retained on a polar substrate, such as a cotton wick. The present disclosure contemplates buffering the carrier oil with a small amount of a stabilizing buffer formula—usually less than 0.1% v/v or w/w. The buffer formula may vary with the $pK_a$ of the solubilized organic acid. Additionally, one or more buffers may be used. For example, two buffers may be employed to create a basin of stability around the solubilized target compound. This is important in the event of contamination, for example, when MCT oil is added to the cartridge of an ENDS or when the reservoir of the ENDS contains a residual volume of a previous vaping liquid.

In addition to buffers, other stabilizing compounds may be added to the carrier oil depending on the target compound. For example, organic bases, organic acids, buffers, etc. may be used. In the case of a target compound that is an organic acid, it may be desirable to add a stabilizer, such as a buffer, to fix the pH of the solution at or around at least 1 pH point below the $pK_a$ of the target compounds in order to ensure that no acidic target compounds are ionized. Alternatively, stabilization may be acidification, without the use of a buffer. For example, an organic acid may be used in very small amounts (typical less than 0.1% w/w). In the case of a target compound that is an organic base, it may be desirable to add a stabilizer, such as a buffer, to fix the pH of the solution, to minimize interaction with certain wick materials.

The solubility of buffers and organic acids in the carrier oil is another consideration. Most organic acids are not miscible in triglyceride oils, but there is be some degree of solubility for organic acids such as formic and acetic acids. Propionic, butyric and valeric acids possess strong goaty aromas and may be objectionable to consumers. It has been discovered that at least a small amount of buffer, organic acid, and/or organic base may be dissolved in a carrier oil/target compound mix, and that even a small amount of buffer may advantageously provide stability to the target compounds to minimize unwanted deposits on the wick.

0.01-10 mM is usually sufficient for the purposes of stabilizing the target compound in the carrier oil.

Organic acids possessing some solubility in triglyceride oils include: valeric acid, caproic acid, caprylic acid, capric acid, benzoic acid, lauric acid, Myristic acid, palmitic acid and stearic acid.

An aspect of the invention may include buffers with some solubility in the carrier oil. Benzoic acid may be useful for stabilizing target compounds in the present disclosure. The pKa of Benzoic acid is about 4.2 with solubility in the carrier oil of approximately 4 gm/100 g and log P (partition co-efficient) of about 1.9. It is typically employed at a level of 0.01 to 0.1% by weight. In use, the raw carrier oil is heated to 85-100 degrees Celsius for 10 minutes. The benzoic acid is then added with stirring and the heat is maintained for about 5 minutes. This may be a typical first step in the preparation of the target compound-carrier oil complexation. This pre-heating of the carrier oil allows any residual moisture to be driven off before the addition of benzoic acid. In some cases of use, the flavor of benzoic acid is cloying. In those cases, phenylacetic acid may be used which possesses a honey-like aroma. It has a pKa and log P comparable to benzoic acid and can be complexed in a similar manner.

Benzyl alcohol may be added to the carrier oil in small amounts (for example, 0.01% to 5%) to improve the clarity and solubility of many target compounds. In addition this method can improve the solubility and clarity of room-temperature solid organic acids such as lauric, myristic and palmitic acids, buffers listed above and room-temperature solid terpenes such as certain diterpenes, sesquiterpenes and triterpenes as well as the terpenoids. In fact, small amounts of benzyl alcohol can improve buffer solubility of weakly acidic buffers in the carrier oil with good stability (low tendency to form esters) so long as no inorganic acids are present.

According to another aspect, compounds may be added to further stabilize the carrier oil. For example, free radical processes can degrade triglycerides. This can cause changes in the stability of the vape oil. In some cases, such as where solubilized compounds bring labile hydroxyl groups and moisture in contact with MCTs, saponification can occur. According to one aspect, drying of a carrier and/or components and choice of compounds can limit the occurrence of moisture. The avoidance of hygroscopic compounds and compounds that form moisture when they break down, and/or the inclusion of compounds that absorb moisture or interfere with hydrolysis make increase stability. In general the stabilization of pH to ensure non-ionized triglycerides helps to control rancidification and saponification, but some target components may require the addition of certain reducing compounds. Filtering oil during blending of components, such as through a small amount of borax or sodium borohydride may improve stability. The inclusion of oil miscible anti-oxidants, such as lutein, lycopene and ascorbyl palmitate, may further improve stability.

Exposure to sunlight or UV light may also cause breakdown. Thus, small amounts of USP singlet-quenching compounds, such as lycopene (more effective for excited singlet suppression than vitamin-E), may be used to reduce the formation of free radicals. Reducing the life of excited singlet-states can reduce the formation of long-lived triplet radicals by reducing intersystem-crossing.

The process for solubilizing target compounds according to the disclosure comprises, in particular, the following steps: (a) preparation of a carrier liquid solution comprising a mixture of medium-chain triglycerides, an amount of this carrier liquid solution is used, the amount depending on the amount of target compound to be solubilized; (b) admixing the carrier liquid solution with the target compound; (c) and, optionally, admixing a stabilizing compound to the carrier liquid/target compound. In some cases, depending on the compound to be solubilized, solvents that dissolve both polar and non-polar compounds such as ethanol, methanol, acetonitrile, 1-butanol or isopropyl alcohol, may be added to encourage solubilization, and then removed by vacuum evaporation. As another aspect, during compounding, dry inert gas may be filtered through the mixture to remove moisture.

Examples

The present disclosure contemplates many types of carrier oils and non-polar target compounds. The range of compounds that may be effectively used in ENDS is vastly expanded as a result of using the non-polar carrier oil described herein. The following specific examples are given for illustration, and do not limit the scope of the claims.

Riboflavin is known to have poor solubility in aqueous solutions and organic solvents. In vegetable glycerin, propylene glycol and water, the solubility of riboflavin is less than 0.2 mg/ml. It may be desirable to solubilize a higher concentration of riboflavin in an ENDS. Solubility of riboflavin may be improved slightly by alkaline buffering, however this dramatically reduces the stability of riboflavin to time, temperature, and UV light. However, greater solubility may be achieved by heating a mixture of methanol and riboflavin to 55-60 degrees Celsius. This mixture may then be added to MCTs (for example 0.0-6.0% C6, 6.0-60% C8, and/or 6.0-60% C10), homogenized for 5 minutes and subsequently heated to approximately 85 degrees Celsius at 250 mb (or 250 hPa) pressure in a rotary evaporator to drive off the methanol. This may achieve an order of magnitude greater solubility for riboflavin in MCTs versus aqueous solutions.

Another example may be sulbutiamine. Sulbutiamine is a disulfide dimer of thiamine. It is insoluble in aqueous solutions but highly soluble in fats. It may be desirable to provide sulbutiamine in an ENDS. For example, a stable solution of 200 mg/mL sulbutiamine in MCTs (for example, 0.0-6.0% C6, 6.0-60% C8, and/or 6.0-60% C10) may be created by simple stirring the solution at 85 degrees Celsius for 5 minutes. Solutions of higher concentration may be possible, for example, by using the method described above (using one or more solvents that dissolve both polar and non-polar compounds such as ethanol, methanol, acetonitrile, 1-butanol or isopropyl alcohol, may be added to encourage solubilization, and then removing the solvent(s) by vacuum evaporation).

Another example may be cannabidiol, which is currently being researched as an investigative new drug by GW Pharmaceuticals, for use in seizure conditions and other diseases. Should GW Pharmaceutical be granted further approval for cannabidiol, or should cannabidiol receives wider approval status, it may be medically desirable for certain patients to receive cannabidiol from an ENDS in vapor form, since this provides arguably the fastest non-invasive route of delivery. Cannabidiol may be solubilized up to about 80 percent v/v in MCTs (for example 0.0-6.0% C6, 6.0-60% C8, and/or 6.0-60% C10) by simply stirring at 45 to 65 degrees Celsius for 5 minutes.

Another example may be diinolylmethane (DIM). DIM is a naturally occurring non-polar compound in cruciferous brassica vegetables. DIM currently has interesting investigative properties in such areas as cancer, infectious diseases, and immune deficiency conditions. In particular, DIM has been investigated for its value in recurrent respiratory papillomatosis, a condition caused by the human papilloma virus. DIM's delivery and bioavailability is limited by its non-polar nature. DIM may be solubilized by admixing 0.01 to 15% with MCT at 65 degrees centigrade. Higher percentages of DIM may be dissolved DIM may be combined with the isoflavone Genistein and prepared in the same manner. The two compounds, taken together, have enhanced value in the inhibition of tumor growth.

Another example may be vitamin-D3, which can simply be admixed in any proportion with the stabilized, viscosity adjusted carrier oil.

Another example may be a combination of oil soluble antioxidants such as lycopene, lutein and ascorbyl palmitate. For example, a stable solution of 200 mg/mL lycopene, lutein, and/or ascorbyl palmitate in MCTs (for example, 0.0-6.0% C6, 6.0-60% C8, and/or 6.0-60% C10) may be created by simple stirring the solution at 85 degrees Celsius for 5 minutes. Solutions of higher concentration may be possible, for example, by using the method described above (using one or more solvents that dissolve both polar and non-polar compounds such as ethanol, methanol, acetonitrile, 1-butanol or isopropyl alcohol, may be added to encourage solubilization, and then removing the solvent(s) by vacuum evaporation).

Another example may be a combination of tocotrienol, alpha-carotene and xanthins, such as Zeaxanthin, Astaxanthin, Crytoxanthin and Canthaxanthin. These are powerful antioxidants that provide benefits in various tissues of the human body. They may be incorporated into the carrier oil by admixing in small quantities (<2 mg/ml) (or in larger quantities using the method described above using one or more solvents that dissolve both polar and non-polar compounds such as ethanol, methanol, acetonitrile, 1-butanol or isopropyl alcohol, may be added to encourage solubilization, and then removing the solvent(s) by vacuum evaporation similar to section 0044, where the solvent to be evaporated may be among those listed or may include among others, ethyl-acetate, dimethylformamide, dichloroethane and trichloroethane).

Another example may be a combination of mono-terpenes, mono-terpenoids, di-terpenes, di-terpenoids and sesquiterpenes. Mono-terpenes are readily soluble in the carrier oil and may simply be admixed in any ratio at temperatures from 10-65 degrees Celsius, depending on the species. Monoterpenoids, diterpenes, diterpenoids and sesquiterpenes may require homogenization, solvent addition and evaporation (using one or more solvents that dissolve both polar and non-polar compounds such as ethanol, methanol, acetonitrile, 1-butanol or isopropyl alcohol, may be added to encourage solubilization, and then removing the solvent(s) by vacuum evaporation).

Terpenes have many desirable effects in human physiology. Linalool improves muscle relaxation. Beta-Caryophyllene reduces pain. Beta-Myrcene can improve the transport of many compounds across the blood-brain barrier. The diterpenoid retinal has benefits as an animal form of vitamin-A.

Monoterpenes, including acyclic monoterpenes, monocyclic monoterpenes, and bicyclic monoterpenes may be solubilized according to the method described herein. For example, a list of exemplary monoterpenes that may be included by admixing at 10-65 degrees Celsius in proportions of 0.0001% to 60% monoterpene in 99.9999% to 40% MCTs includes: Ascaridole; Bornane; Borneol; Camphene; Camphor; Carene; Carvacrol; Carveol; Carvone; Carvonic acid; Chrysanthemic acid; Chrysanthenone; Citral; Citronellal; Citronellol; Cuminaldehyde; P-Cymene; Cymenes; Epomediol; Eucalyptol Fenchol; Fenchone; Geranic acid; Geraniol; Geranyl acetate; Geranyl pyrophosphate; Grapefruit mercaptan; Halomon; Hinokitiol; 8-Hydroxygeraniol; Incarvillateine; (S)-Ipsdienol; Jasmolone; Lavandulol; Lavandulyl acetate; Levoverbenone; Limonene; Linalool; Linalyl acetate; Lineatin; P-Menthane-3,8-diol; Menthofuran; Menthol; Menthone; Menthoxypropanediol; Menthyl acetate; 2-Methylisoborneol; Myrcene; Myrcenol; Nerol; Nerolic acid; Ocimene; 8-Oxogeranial; Paramenthane hydroperoxide; Perilla ketone; Perillaldehyde; Perillartine; Perillene; Phellandrene; Picrocrocin; Pinene; Alpha-Pinene; Beta-Pinene; Piperitone; Pulegone; Rhodinol; Rose oxide; Sabinene; Safranal; Sobrerol; Terpinen-4-ol; Terpinene; Terpineol; Thujaplicin; Thujene; Thujone; Thymol; Thymoquinone; Umbellulone; Verbenone; and Wine lactone.

A list of exemplary diterpenes that may be solubilized at temperatures from 15-85 degrees Celsius, as in section 0044, in proportions from 0.0001% to 60% includes: Abietane; Abietic acid; Agelasimine; Agelasine; Andrographolide; Aphidicolin; Beta-Araneosene; Bipinnatin J; Cafestol; Carnosic acid; Carnosol; Cembrene A; Clerodane diterpene; 10-Deacetylbaccatin; EBC-46; Erinacine; Ferruginol; Fichtelite; Forskolin; Galanolactone; Geranylgeraniol; Geranylgeranyl pyrophosphate; Gibberellin; Ginkgolide; Grayanotoxin; Guanacastepene A; Ingenol mebutate; Isocupressic acid; Isopimaric acid; Isotuberculosinol; Kahweol; KM-233; Labdane; Lagochilin; Laurenene; Leelamine; Levopimaric acid; Menatetrenone; Momilactone B; Neotipterifordin; 18-Norabietane; Panicudine; Phorbol; Phorbol 12,13-dibutyrate; Phyllocladane; Phytane; Phytanic acid; Phytol; Pimaric acid; Pristane; Pristanic acid; Prostratin; Pseudopterosin A; Retinol; Ryanodine; Salvinorin; Sclarene; Sclareol; Shortolide A; Simonellite; Stemarene; Stemodene; Steviol; Taxadiene; Taxamairin A; Taxodone; Tenuifolin; 12-O-Tetradecanoylphorbol-13-acetate; Tetrahydrocannabinol-C4; Tetrahydrocannabinolic acid; Totarol; Tricholomalide; Tripchlorolide; Tripdiolide; Triptolide; and Triptolidenol.

The list of exemplary diterpenoids that may be solubilized at temperatures from 15-85 degrees Celsius, by admixing (or using one or more solvents that dissolve both polar and non-polar compounds such as ethanol, methanol, acetonitrile, 1-butanol or isopropyl alcohol, to encourage solubilization, and then removing the solvent(s) by vacuum evaporation), in proportions from 0.0001% to 60%, is large with hundreds of skeletons and thousands of species (such as retinol, phytol).

A list of exemplary sesquiterpenes that may be solubilized at temperatures from 15-85 degrees Celsius, as in section 0044, in proportions from 0.0001% to 60% includes: Abscisic acid; Amorpha-4,11-diene; Aristolochene; Artemether; Artemotil; Artesunate; Bisabolene; Bisabolol; Botrydial; Cadalene; Cadinene; Alpha-Cadinol; Delta-Cadinol; Capnellene; Capsidiol; Carotol; Caryophyllene; Cedrene; Cedrol; Copaene; Cubebol; Curdione; Curzerene; Curzerenone; Dictyophorine; Drimane; Elemene; Farnesene; Farnesol; Farnesyl pyrophosphate; Germacrene; Germacrone; Guaiazulene; Guaiene; Guaiol; Gyrinal; Hernandulcin; Humulene; Indometacin farnesil; Ionone; Isocomene; Juvabione; Ledol; Longifolene; Mutisianthol; Nardosinone; Nerolidol; Nootkatone; Norpatchoulenol; Onchidal; Patchoulol; Periplanone B; Petasin; Phaseic acid; Polygodial; A-Santalol; B-Santalol; Santonic acid; Selinene;

Spathulenol; Thujopsene; Tripfordine; Triptofordin C-2; Valencene; Velleral; Verrucarin A; Vetivazulene; A-Vetivone; and Zingiberene.

Another example may be the addition of Omega-3 fatty acids by admixing, at temperatures between 15-65 degrees Celsius, to the carrier oil. Specific examples include Eicospentaenoic acid, Docosahexaenoic acid, in proportions from 0.01% to 70%.

Another example may be the addition of fatty acids, such as linoleic and linolenic acid, by admixing at temperatures between 15-65 degrees centigrade, to the carrier oil. Fatty acids are easily rancidified but can be stabilized with methods, such as singlet quenchers and antioxidants described herein.

Another example may be the addition of cannabinoids other than cannabidiol, the diterpene Tetrahydracanabinol and its acid to the carrier oil. Over 100 cannabinoids have been discovered. These can be admixed to the carrier oil at 45 to 65 degrees Celsius for 5 minutes to achieve complete dissolution.

There is thus disclosed a method for solubilizing non-polar target compounds in a carrier liquid suitable for use in an ENDS. It will be appreciated that numerous modifications may be made without departing from the scope and spirit of this disclosure. The appended claims are intended to cover such modifications.

What is claimed is:

1. A method for solubilizing a non-polar target compound, wherein the non-polar target compound comprises at least one selected from the group of tetrahydrocannabinolic acid, tetrahydrocannabinol-C4 and tetrahydrocannabinol, the method comprising:
    admixing the non-polar target compound and a medium chain triglyceride carrier liquid comprised of at least one of 0-6.0% of the triglyceride form of hexanoic acid, 6.0-60% of the triglyceride form of octanic acid, and 6.0-60% of the triglyceride form of decanoic acid to form an azeotropic solution;
    adding an amount of buffer to the carrier liquid; and
    heating the azeotropic solution in a heated vaporization delivery system to vaporize the azeotropic solution.

2. The method of claim 1, wherein the carrier liquid and the non-polar target compound are mixed in a ratio of about 50:50 v/v.

3. The method of claim 1, wherein the method further comprises adding an amount of acid to the carrier liquid.

4. The method of claim 1, wherein the method further comprises adding an amount of two or more buffers to the carrier liquid.

5. The method of claim 1, wherein the buffer has a molar concentration of around 0.01-10 mM in the carrier liquid.

6. The method of claim 1, wherein the carrier liquid and the non-polar target compound are mixed in a ratio of about 0.01:99.99 v/v.

7. The method of claim 1, wherein the carrier liquid and the non-polar target compound are mixed in a ratio of about 95:5 v/v.

8. The method of claim 1, wherein admixing the medium chain triglyceride carrier liquid and the non-polar target compound forms an azeotropic mixture, wherein the carrier liquid and the non-polar target compound are mixed in a ratio of about 50:50 v/v, and wherein the method further comprises adding at least one buffer to the carrier liquid, wherein the at least one buffer a molar concentration of around 0.01-10 mM in the carrier liquid.

9. The method of claim 8, further comprising the step of adding an oil miscible anti-oxidant to the carrier liquid.

10. A composition for use in an electronic nicotine delivery system, the composition comprising:
    a non-polar target compound, the non-polar target compound comprising at least one selected from the group of tetrahydrocannabinolic acid, tetrahydrocannabinol-C4 and tetrahydrocannabinol;
    a carrier liquid comprised of one or more medium chain triglycerides comprised of at least one of about 0-6.0% of the triglyceride form of hexanoic acid, about 6.0-60% of the triglyceride form of octanic acid, and about 6.0-60% of the triglyceride form of decanoic acid; and
    at least one buffer having a molar concentration of around 0.01-10 mM in the carrier liquid.

11. The composition of claim 10, wherein the non-polar target compound comprises tetrahydrocannabinol.

12. The composition of claim 10, wherein the composition comprises approximately 40 to 60 percent non-polar target compound and 40 to 60 percent carrier liquid.

13. The composition of claim 10, wherein the carrier liquid comprises a mixture of at least two or more of the triglyceride forms of: hexanoic acid, octanic acid, decanoic acid, and dodecanoic acid.

14. The composition of claim 10, wherein the composition comprises an azeotropic mixture having an azeotropic temperature of vaporization, and wherein the azeotropic temperature of vaporization is lower than a temperature of vaporization of the non-polar target compound and lower than a temperature of vaporization of carrier liquid.

15. The composition of claim 14, wherein the composition comprises approximately 40 to 60 percent non-polar target compound and 40 to 60 percent carrier liquid, and wherein the carrier liquid comprises an azeotropic mixture of the carrier liquid.

16. The composition of claim 10, further comprising an oil miscible anti-oxidant.

17. A vapor cartridge for use in a heated vaporization system, the vapor cartridge containing a composition comprising;
    a non-polar target compound, the non-polar target compound comprising at least one selected from the group of tetrahydrocannabinolic acid, tetrahydrocannabinol-C4 and tetrahydrocannabinol;
    at least one buffer; and
    a carrier liquid comprised of one or more medium chain triglycerides comprised of at least one of the triglyceride forms of 0-6.0% hexanoic acid, 6.0-60% octanic acid, and 6.0-60% decanoic acid.

18. The vapor cartridge of claim 17, further comprising an oil miscible anti-oxidant.

19. The vapor cartridge of claim 17, wherein the non-polar target compound comprises tetrahydrocannabinol.

\* \* \* \* \*